(12) United States Patent
Askenazi et al.

(10) Patent No.: US 10,969,330 B2
(45) Date of Patent: Apr. 6, 2021

(54) METHOD FOR DETERMINING THE COLOR OF A COSMETIC PRODUCT ON A SKIN MODEL

(71) Applicant: L'OREAL, Paris (FR)

(72) Inventors: Benjamin Askenazi, Asnieres-sur-Seine (FR); Johan Aubert, Asnieres-sur-Seine (FR)

(73) Assignee: L'OREAL, Paris (FR)

( * ) Notice: Subject to any disclaimer, the term of this patent is extended or adjusted under 35 U.S.C. 154(b) by 418 days.

(21) Appl. No.: 16/087,299

(22) PCT Filed: Mar. 23, 2017

(86) PCT No.: PCT/EP2017/056979
§ 371 (c)(1),
(2) Date: Sep. 21, 2018

(87) PCT Pub. No.: WO2017/162818
PCT Pub. Date: Sep. 28, 2017

(65) Prior Publication Data
US 2019/0107481 A1 Apr. 11, 2019

(30) Foreign Application Priority Data
Mar. 23, 2016 (FR) ...................................... 1652487

(51) Int. Cl.
*G01N 21/25* (2006.01)
*G01N 21/47* (2006.01)
(Continued)

(52) U.S. Cl.
CPC ............. *G01N 21/25* (2013.01); *A45D 44/00* (2013.01); *A45D 44/005* (2013.01);
(Continued)

(58) Field of Classification Search
CPC ............... G01N 21/25; G01N 21/4738; G01N 2021/8405; A45D 44/00; A45D 44/005; A45D 2044/007; A61B 5/441
(Continued)

(56) References Cited

U.S. PATENT DOCUMENTS 7,820,150 B2 * 10/2010 Kohlhase ............... A61K 8/342
424/70.28
9,168,209 B2 * 10/2015 Ballesteros .......... A61K 8/0245
(Continued)

FOREIGN PATENT DOCUMENTS

WO    WO 2014/204007 A1    12/2014

OTHER PUBLICATIONS

Koirala et al: "Color mixing and color separation of pigments with concentration prediction", Color Research & Application, vol. 33, No. 6, Dec. 2008 (Dec. 2008), pp. 461-469, XP055322473.
(Continued)

*Primary Examiner* — David P Porta
*Assistant Examiner* — Gisselle M Gutierrez
(74) *Attorney, Agent, or Firm* — Polsinelli PC

(57) ABSTRACT

The invention relates to a method for determining the color of a cosmetic product on a skin model, the method including steps to: —for a plurality of wavelengths, supply experimental points giving diffusion and/or absorption values for several mixes of a given concentration of one pigment in another pigment, each mix corresponding to different given concentrations, and —use a physicochemical model capable of predicting interactions between pigments passing through experimental points to obtain the curve giving the diffusion and/or absorption for each wavelength as a function of the given concentration of pigment in the mix of pigments considered.

20 Claims, 1 Drawing Sheet

Figure 1:
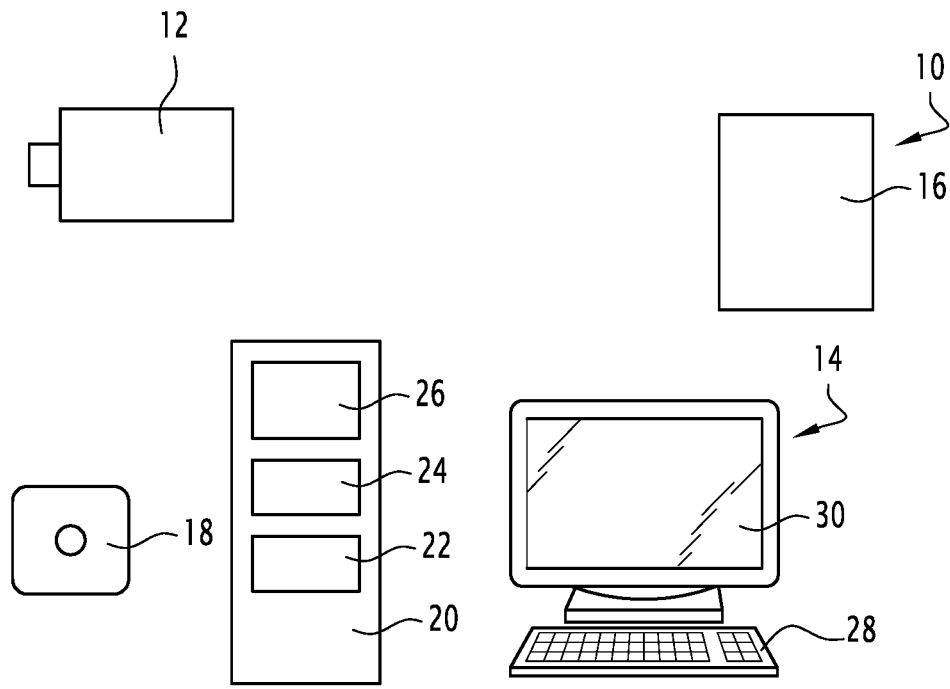

(51) Int. Cl.
  *A45D 44/00* (2006.01)
  *G01N 21/84* (2006.01)
  *A61B 5/00* (2006.01)

(52) U.S. Cl.
  CPC ... *G01N 21/4738* (2013.01); *A45D 2044/007* (2013.01); *A61B 5/441* (2013.01); *G01N 2021/8405* (2013.01)

(58) Field of Classification Search
  USPC .......................................................... 702/19
  See application file for complete search history.

(56) References Cited

U.S. PATENT DOCUMENTS

| | | | | |
|---|---|---|---|---|
| 9,168,393 | B2 * | 10/2015 | Ballesteros | A61K 8/29 |
| 9,168,394 | B2 * | 10/2015 | Ballesteros | A61K 8/29 |
| 9,320,687 | B2 * | 4/2016 | Ballesteros | A61Q 1/02 |
| 2004/0057915 | A1 * | 3/2004 | Gers-Barlag | A61K 8/29 |
| | | | | 424/59 |
| 2019/0090614 | A1 * | 3/2019 | Askenazi | G01J 3/50 |

OTHER PUBLICATIONS

Hu et al: "Concentration additivity of coefficients for maxillofacial elastomer pigmented to skin colors", Dental Materials, vol. 25, No. 11, Nov. 2009 (Nov. 2009), pp. 1468-1473, XP026665470.
Doi et al: "Spectral Estimation of Skin Color with Foundation Makeup", Jun. 28, 2005 (Jun. 28, 2005), Image Analysis, pp. 95-104, XP019010978.
Li et al: "Simulating makeup through physics-based manipulation of intrinsic image layers", 2015 IEEE Conference on Computer Vision and Pattern Recognition (CVPR), IEEE, Jun. 7, 2015 (Jun. 7, 2015), pp. 4621-4629, XP032793919.
Kubelka et al: "Ein Beitrag Zur Optik Der Farbanstriche", Zeitschrift Fuer Technische Physik, vol. 12, No. 11A, 1931, pp. 593-601, XP001023740.
Saunderson: "Calculation of the Color of Pigmented Plastics", Journal of the Optical Society of America, vol. 32, No. 12, Dec. 1942 (Dec. 1942), p. 727, XP055322620.
Duncan: "The colour of pigment mixtures", Proceedings of the Physical Society, 1940, pp. 390-401, XP055322637.

* cited by examiner

METHOD FOR DETERMINING THE COLOR OF A COSMETIC PRODUCT ON A SKIN MODEL

CROSS REFERENCE TO RELATED APPLICATIONS

This application is the National Phase of Application No. PCT/EP2017/056979 filed Mar. 23, 2017, and claims the priority of Application No. 1652487 filed in France on Mar. 23, 2016. The entire contents of each application are hereby incorporated by reference.

This invention relates to a method for determining the color of a cosmetic product on a skin model This invention also relates to an associated computer program.

A trend in cosmetics is towards customization of the cosmetic product to suit the wearer. Color is one parameter of such customization.

Furthermore, wearers increasingly feel the need to adapt the cosmetic product to match the color of their skin.

Wearers call upon makeup experts for this purpose. These specialists discuss with the wearer and suggest a sample of a cosmetic product that appears to be suited to the wearer's skin color. The wearer tests the proposed sample. If the wearer is satisfied, the wearer orders a larger packaging of the cosmetic product. Otherwise, a new sample is suggested until the wearer is satisfied.

However, in practice such a method is long because the wearer satisfaction rate on presentation of the first sample is relatively low (of the order of 5% even when some steps are automated using a special-purpose machine).

Therefore there is a need for a method by which the wearer's satisfaction rate can be improved on presentation of a first sample of the cosmetic product adapted to the wearer's skin color.

The description also describes a method of determining the color of a cosmetic product on a skin model, the method including steps to supply the composition of pigments in the cosmetic product, the composition comprising at least two pigments including at least one colored pigment, for a plurality of wavelengths, supply of experimental points giving diffusion and/or absorption values for several mixes of a given concentration of one pigment in another pigment, each mix corresponding to different given concentrations, use of a physicochemical model capable of predicting interactions between pigments passing through experimental points to obtain the curve giving the diffusion and/or absorption for each wavelength as a function of the given concentration of pigment in the mix of pigments considered, the physicochemical model for example being an interpolation of experimental points, calculation of the diffusion and/or absorption curve of the cosmetic product using the curves obtained, deduction of the diffuse reflectivity of the cosmetic product on a skin model from the curve giving the diffusion and/or absorption, and obtaining the color of the cosmetic product on a skin model using the deduced diffuse reflectivity.

According to particular embodiments, the determination method comprises one or several of the following characteristics taken in isolation or in any technically possible combination:

in the supply step, the experimental products are obtained on a skin model.

the deduction step includes the use of a colorimetric model to obtain the diffuse reflectivity, the colorimetric model for example being a Kubelka-Munk model corrected using Saunderson corrections.

the color is obtained based on integrations of the diffuse reflectivity.

the calculation step includes the calculation of the diffusion and/or absorption curve of a mix of a colored pigment in one or several other pigments, for each colored pigment.

the calculation includes the determination of compositions of three binary mixes of pigments obtained in the absence of another pigment in the mix of the colored pigment and the other pigment(s), determination of the diffusion and/or absorption value of each binary mix using the curve obtained, and determination of the diffusion and/or absorption value for the mix of colored pigment and/or other pigments by calculating an average of three determined values.

when the composition includes several colored pigments, the calculation step includes a weighted addition for each colored pigment on the diffusion and/or absorption curve of a mix of the colored pigment and the one or more other pigments, the weighting depending on the relative quantity of colored pigment.

the method includes the supply of more than four points per mix.

the points are equally distributed at given concentration.

The description also relates to a computer program comprising a legible information support on which a computer program is stored containing program instructions, the computer program being loadable onto a data processing unit and adapted to implement a method of determination as described above when the computer program is installed on the data processing unit.

The description also describes a method of determining the color of a cosmetic product adapted to the skin of a wearer of the cosmetic product, the method including the following steps:

supply data related to the appearance of the wearer's skin, determine the color of the cosmetic product by using a correspondence function applied to data about the appearance of the wearer's skin, the correspondence function associating a wearer's skin color with a color of the cosmetic product, the correspondence function having at least three reference associations, a reference association associating a predetermined cosmetic product color with a predetermined wearer skin color within a tolerance, the tolerance being equal to a distance of 2 in the CIE L*a*b* color space and the at least three associations being chosen from the group of associations composed of:

a first association associating the color of the cosmetic product with coordinates in the CIE L*a*b* color space equal to (26.9; 10.7; 13.6) with a wearer's skin color with coordinates in the CIE L*a*b* color space equal to (27.0; 12.4; 11.6), a second association associating the color of the cosmetic product with coordinates in the CIE L*a*b* color space equal to (37.6; 10.8; 15.1) with a wearer's skin color with coordinates in the CIE L*a*b* color space equal to (37.6; 11.0; 14.2), a third association associating the color of the cosmetic product with coordinates in the CIE L*a*b* color space equal to (50.2; 15.4; 22.9) with a wearer's skin color with coordinates in the CIE L*a*b* color space equal to (50.2; 13.2; 25.1), a fourth association associating the color of the cosmetic product with coordinates in the CIE L*a*b* color space equal to (51.2; 13.5; 22.1) with a wearer's skin color with coordinates in the CIE L*a*b* color space equal to (51.2; 11.3; 23.6),
a fifth association associating the color of the cosmetic product with coordinates in the CIE L*a*b* color space equal to (63.0; 12.9; 18.0) with a wearer's skin color with coordinates in the CIE L*a*b* color space equal to (6.0; 8.45; 19.5),
a sixth association associating the color of the cosmetic product with coordinates in the CIE L*a*b* color space equal to (63.1; 12.4; 22.8) with a wearer's skin color with coordinates in the CIE L*a*b* color space equal to (63.0; 8.84; 23.5),
a seventh association associating the color of the cosmetic product with coordinates in the CIE L*a*b* color space equal to (66.4; 12.6; 15.0) with a wearer's skin color with coordinates in the CIE L*a*b* color space equal to (66.4; 10.7; 14.9), and
an eighth association associating the color of the cosmetic product with coordinates in the CIE L*a*b* color space equal to (68.6; 8.78; 13.9) with a wearer's skin color with coordinates in the CIE L*a*b* color space equal to (68.6; 5.16; 13.0).

According to particular embodiments, the determination method comprises one or several of the following characteristics taken in isolation or in any technically possible combination:

the correspondence function has at least five reference associations, each reference association associating a predetermined cosmetic product color with each predetermined wearer's color, within a tolerance, the at least five associations being chosen from the group of associations.

the correspondence function has eight reference associations, each reference association associating a predetermined cosmetic product color with each predetermined wearer's color, within a tolerance, the eight associations being chosen from the group of associations.

the tolerance is equal to a distance of 1.5 in the CIE L*a*b* color space.

skin data are spectrometric measurements made on one or several areas of the wearer's skin.

the number of skin areas is greater than or equal to 3.

The description also describes a method of manufacturing a cosmetic product adapted to the skin of a wearer of the cosmetic product, including steps to determine the color of the cosmetic product adapted for the wearer's skin by the use of a determination method like that described above, determination of the composition of pigments in the cosmetic product using a model associating the color of the cosmetic product with a composition of pigments in the cosmetic product to obtain a determined composition, and manufacturing of the cosmetic product from the determined composition.

According to one particular embodiment, the model is obtained by inversion of a link associating a composition of pigments in the cosmetic product with a color of the cosmetic product, the link being obtained using a method of determining the color of a cosmetic product on a skin model for several distinct compositions, the method for determining the color including steps to supply the composition of pigments in the cosmetic product, the composition comprising at least two pigments including at least one colored pigment, for a plurality of wavelengths, supply of experimental points giving diffusion and/or absorption values for several mixes of a given concentration of one pigment in another pigment, each mix corresponding to different given concentrations, use of a physicochemical model capable of predicting interactions between pigments passing through experimental points to obtain the curve giving the diffusion and/or absorption for each wavelength as a function of the given concentration of pigment in the mix of pigments considered, the physicochemical model for example being an interpolation of experimental points, calculation of the diffusion and/or absorption curve of the cosmetic product using the curves obtained, deduction of the diffuse reflectivity of the cosmetic product on a skin model from the curve giving the diffusion and/or absorption, and obtaining the color of the cosmetic product on a skin model using the deduced diffuse reflectivity.

The description also relates to a computer program comprising a legible information support on which a computer program is stored containing program instructions, the computer program being loadable onto a data processing unit and adapted to implement a method of determination as described above when the computer program is installed on the data processing unit.

The description also describes a device for manufacturing a cosmetic product adapted to the skin of a wearer of the cosmetic product, the device including a controller capable of determining the color of the cosmetic product adapted for the wearer's skin by the use of a determination method like that described above, and determining the composition of pigments in the cosmetic product using a model associating the color of the cosmetic product with a composition of pigments in the cosmetic product to obtain a determined composition, and a manufacturing unit for the cosmetic product from the determined composition.

Figure 2:
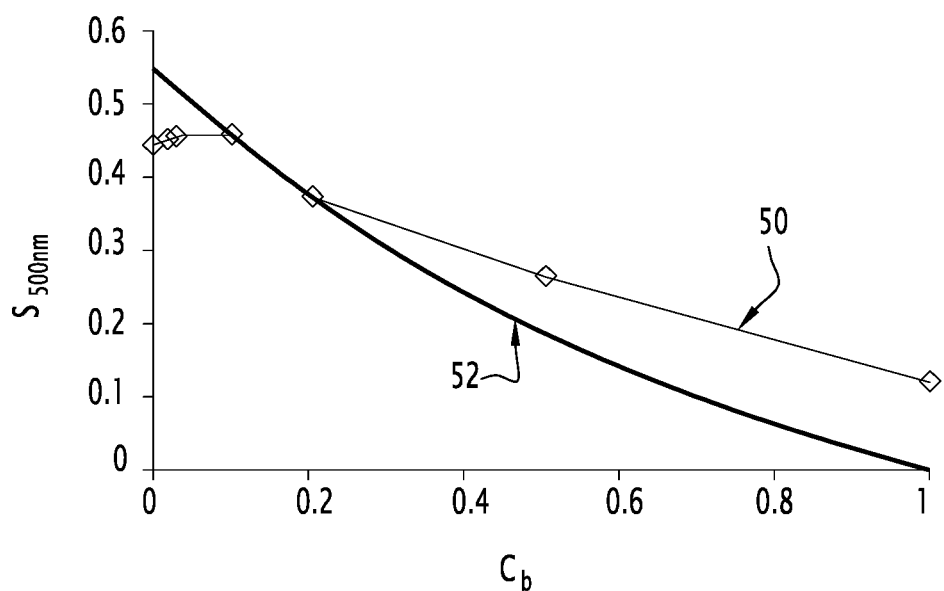

Other characteristics and advantages of the invention will appear when reading the following description of an embodiment of the invention, provided solely as an example and with reference to the drawings which are:

FIG. 1, a diagrammatic view of a manufacturing device, and;

FIG. 2, a graph comparing the variation of diffusion of several dilutions of a binary mix of pigments in the case of the invention and in the case of the state of the art.

A device 10 for manufacturing a cosmetic product is illustrated on FIG. 1.

By definition, a cosmetic product is any substance or a preparation intended to be placed in contact with surface portions of the human body (the epidermis, hair and nail system, lips and external genital organs), or with the teeth and the mucous membranes of the oral cavity with a view exclusively or mainly of cleaning them, perfuming them, modifying the aspect of them, protecting them, maintaining them in good condition or correcting body odors.

The color of the cosmetic product is adapted for a skin color of a wearer of the cosmetic product.

For example, the cosmetic product is a foundation or a lipstick.

The term "color" for the cosmetic product refers to the apparent color or rendering once the cosmetic product has been applied to skin or to a skin model.

The device 10 comprises a measurement sensor 12, a controller 14 and a manufacturing unit 16.

The measurement sensor 12 is capable of taking pictures of areas on the carrier.

According to one embodiment, the measurement sensor 12 also comprises an analysis tool capable of extracting images of spectrometric measurements.

The controller 14 is capable of interacting with a computer program 18. The interaction between the computer program 18 and the controller 14 makes it possible to implement a method for determining the color of a cosmetic product adapted to a skin of a wearer of the cosmetic product and to determine the composition of pigments in the cosmetic product using a model associating the color of the cosmetic product with a composition of pigments in the cosmetic product to obtain a determined composition.

The controller 14 is a computer.

More generally, the controller 14 is an electronic computer capable of manipulating and/or transforming data represented as electronic or physical quantities in registers of the controller 14 and/or memories into other similar data corresponding to physical data in memories, registers or other types of display, transmission or storage devices.

The controller 14 comprises a processor 20 including a data processing unit 22, memories 24 and an information support drive 26. The controller 14 also comprises a keyboard 28 and a display unit 30.

The computer program 18 comprises a legible information support.

A legible information support is a support that can be read by the controller 14, usually by the data processing unit 22. The legible information support is a medium capable of memorizing electronic instructions and capable of being coupled to a bus of a computer system.

For example, the legible information support is a diskette or floppy disk, an optical disk, a CD-ROM, a magneto-optical disk, a ROM memory, a RAM memory, an EPROM memory, an EEPROM memory, a magnetic card or an optical card.

A computer program containing program instructions is stored on the legible information support.

The computer program can be loaded on the data processing unit 20 and is adapted to control the use of a procedure for the identification of a relation between physical elements when the computer program is used on the data processing unit 20.

The manufacturing unit 16 is capable of manufacturing a cosmetic product from the determined composition.

The operation of device 10 is now described with reference to a method of manufacturing a cosmetic product.

The method of manufacturing the cosmetic product comprises two phases: a first phase to determine the color of the cosmetic product adapted to the wearer and a second phase to manufacture the cosmetic product capable of obtaining the determined color.

The first color determination phase includes a step to supply data and a determination step.

In the data supply step, data about the wearer's skin color are supplied.

Data related to the wearer's skin color include for example spectrometric measurements made on several zones of the wearer's skin.

For example, such spectrometric measurements are made by a makeup specialist when the wearer and the makeup specialist meet.

For example, the makeup specialist uses a portable spectrometer or the measurement sensor 12.

According to one embodiment, the makeup specialist makes measurements on 3 or more skin areas.

According to another embodiment, the makeup specialist makes measurements on only one skin area, for example corresponding to the wearer's entire face.

According to another example, the data related to the wearer's skin color are colorimetric values, obtained for example using the previously described spectrometric measurements.

In the following, colorimetric values are presented in the CIE L*a*b* color space.

The CIE L*a*b* color space, often abbreviated CIELAB, is a color space for surface colors defined by the Commission Internationale de l'Eclairage (CIE) in 1976. It is based on evaluations of the CIE XYZ system, and abandons linearity to more accurately show up differences between colors perceived by the human eye. Three magnitudes characterize colors in this model, namely the lightness L* derived from the luminance (Y) of the XYZ evaluation, and two parameters a* and b* that express the color difference from the color of a gray surface with the same lightness, as the chrominance of the video. The definition of a gray, uncolored, achromatic surface implies that the composition of the light that illuminates the colored surface is explicitly indicated. This illuminant is often daylight corresponding to the D65 normalized standard.

Any other color space could be envisaged.

More generally, any means of associating spectra could also be used in this context.

It is assumed in the following that the supplied data are colorimetric values.

If the supplied data are not colorimetric values, a conversion step is applied during the supply step.

Thus, at the end of the supply step, the color of the wearer's skin is colorimetrically known.

In the determination step, the color of the cosmetic product is determined by using a correspondence function applied to data related to the wearer's skin color.

In a simplified manner, data related to the wearer's skin color can be used to obtain colorimetric values of the color of the cosmetic product adapted to the wearer, making use of a conversion made by the correspondence function.

The correspondence function associates a color of a cosmetic product applied to a wearer's skin color.

In the special case of the face, the color of the cosmetic product applied to this skin color is called the "global face color appearance".

In the following, the color of the cosmetic product applied on this skin color is simply called the "cosmetic product color".

This means that the image of a wearer's skin color by the correspondence function is a cosmetic product color.

More precisely, a cosmetic product color is associated with areas of the wearer's skin color by the correspondence function.

The correspondence function used is specific and is derived from experiments performed by the applicant.

The correspondence function has at least three reference associations.

By definition, a reference association associates a predetermined cosmetic product color with a predetermined wearer's skin color, within a tolerance.

The expression "within a tolerance" refers to a tolerance in the image space and in the object space.

It also means that firstly, the image of the predetermined wearer's skin color is a color that is the same as color of the predetermined cosmetic product, within the tolerance.

Furthermore, it also means that the reference association skin color is the same as the predetermined wearer's skin color, within the tolerance.

Consequent, a reference association associates at least one point satisfying the tolerance relation with the predetermined wearer's skin color, with at least one point satisfying the tolerance relation with the predetermined cosmetic product color.

For example, the tolerance is expressed in the CIE L*a*b* color space.

According to one example, the tolerance is equal to a distance of 2 in the CIE L*a*b* color space.

According to another example, the tolerance is equal to a distance of 1.5 in the CIE L*a*b* color space.

The three associations are chosen among a group of associations composed of the eight associations described below.

The first association associates the color of the cosmetic product with coordinates in the CIE L*a*b* color space equal to (26.9; 10.7; 13.6) with a wearer's skin color with coordinates in the CIE L*a*b* color space equal to (27.0; 12.4; 11.6). In practice, the first association corresponds to a skin qualified as "deep dark".

The second association associates the color of the cosmetic product with coordinates in the CIE L*a*b* color space equal to (37.6; 10.8; 15.1) with a wearer's skin color with coordinates in the CIE L*a*b* color space equal to (37.6; 11.0; 14.2). In practice, the second association corresponds to a skin qualified as "dark".

The third association associates the color of the cosmetic product with coordinates in the CIE L*a*b* color space equal to (50.2; 15.4; 22.9) with a wearer's skin color with coordinates in the CIE L*a*b* color space equal to (50.2; 13.2; 25.1). In practice, the third association corresponds to a skin qualified as "medium 1".

The fourth association associates the color of the cosmetic product with coordinates in the CIE L*a*b* color space equal to (51.2; 13.5; 22.1) with a wearer's skin color with coordinates in the CIE L*a*b* color space equal to (51.2; 11.3; 23.6). In practice, the fourth association corresponds to a skin qualified as "medium 2".

The fifth association associates the color of the cosmetic product with coordinates in the CIE L*a*b* color space equal to (63.0; 12.9; 18.0) with a wearer's skin color with coordinates in the CIE L*a*b* color space equal to (6.0; 8.45; 19.5). In practice, the fifth association corresponds to a skin qualified as "light".

The sixth association associates the color of the cosmetic product with coordinates in the CIE L*a*b* color space equal to (63.1; 12.4; 22.8) with a wearer's skin color with coordinates in the CIE L*a*b* color space equal to (63.0; 8.84; 23.5). In practice, the sixth association corresponds to a skin qualified as "golden".

The seventh association associates the color of the cosmetic product with coordinates in the CIE L*a*b* color space equal to (66.4; 12.6; 15.0) with a wearer's skin color with coordinates in the CIE L*a*b* color space equal to (66.4; 10.7; 14.9). In practice, the seventh association corresponds to a skin qualified as "pink".

The eighth association associates the color of the cosmetic product with coordinates in the CIE L*a*b* color space equal to (68.6; 8.78; 13.9) with a wearer's skin color with coordinates in the CIE L*a*b* color space equal to (68.6; 5.16; 13.0). In practice, the eighth association corresponds to a skin qualified as "fair".

Use of the correspondence function can give a cosmetic product color adapted to the wearer's skin color.

With knowledge of such data, the specialist can obtain the right cosmetic product more quickly.

This effect can be improved if the correspondence function includes at least five reference associations among the group of associations.

According to another embodiment, the correspondence function has the eight reference associations.

As a variant, the correspondence function has even more reference associations.

According to another variant, the correspondence function uses the fifth association.

According to another variant or in addition, the correspondence function is piecewise continuous between the reference associations.

However, it should be noted that with the eight reference associations, all major skin types are represented so that a good compromise can be obtained between the experimental determination of the correspondence function and the required precision for the method.

The second phases includes an application step and a manufacturing step of the cosmetic product.

In the application step, a model experimentally produced with the color of the determined cosmetic product is applied to obtain the composition of pigments in the associated cosmetic product.

The method by which this model is produced is described in the remainder of this application.

The application step gives the pigment composition of the required cosmetic product.

For example, the composition is expressed as a percentage of pigments by mass.

During the manufacturing step, the cosmetic product is manufactured using the given composition of pigments by mass.

The manufacturing method can thus be used to manufacture a cosmetic product adapted to the wearer's skin color.

The result is that the wearer's satisfaction rate on presentation of the first sample is relatively high (of the order of 80%).

The method of producing a model to associate a cosmetic product color with a composition of pigments is explained by describing a method of determining the color of a cosmetic product on a skin model.

The determination method can create a link between the cosmetic product color on a skin model and a cosmetic product composition. This link is the inverse of the model used in the manufacturing method.

The determination method includes a first supply step, a second supply step, an interpolation step; a calculation step, a deduction step and a production step.

In the first supply step, the composition of pigments in the cosmetic product is supplied, the composition including at least one white pigment, one black pigment and at least one colored pigment.

As explained above, the composition is expressed for example as a percentage of pigments by mass.

The number of colored pigments is usually less than or equal to 2.

For example, a foundation composition is expressed with only two colored pigments, namely the red pigment and the yellow pigment.

The second supply step is applied for a plurality of wavelengths.

For example, the second supply step is used for a number of between 10 and 30 distinct wavelengths.

According to one embodiment, the wavelengths are equally distributed on the visible spectral band varying from 400 nanometers to 800 nanometers.

For each wavelength, experimental values are supplied giving diffusion and/or absorption values for several mixes of a given concentration of one pigment in another pigment. Such a mix is qualified as binary in the remainder of the description.

Experimental points correspond to the same mix application thickness, the thickness corresponding to a realistic usage case, in other words a case in which neither too little nor too much mix is applied.

One of the two pigments is a black or white pigment.

Furthermore, each mix corresponds to different given concentrations. In other words, each mix corresponds to different dilutions of one pigment in another pigment.

Diffusion and/or absorption values are for example derived from experiments carried out on supports forming skin models.

According to one embodiment, the mixes considered include all possible mixes in which one of the two pigments is a black or white pigment, eliminating symmetric mixes (a given pigment diluted in another pigment is then considered as being the same mix as a mix of the other pigment in the given pigment).

For example, in the case of a foundation, the types of binary mixes are the mix of red pigment in white pigment, red in back, white in black, white in yellow, black in yellow.

According to one embodiment, more than four points per mix are supplied in the second supply step.

For example, eight points are supplied for each mix.

According to one embodiment, the points are equally distributed at a given concentration. This means that experimental points correspond to equally distributed dilution ratios between 0 and 100, for example every 20.

In the interpolation step, the experimental points are interpolated to obtain the curve giving the diffusion and/or absorption for each wavelength as a function of the given concentration of pigment in the mix of pigments considered.

For example, in the example illustrated in FIG. 2, the interpolation is piecewise linear, in other words each experimental point is connected to is closest neighbors by a straight line. The curve obtained is marked as reference 50 on FIG. 2.

According to the applicant's tests, this is most promising interpolation in terms of calculation time during implementation of the determination process. The interpolated curve 50 can also give a curve with a much better precision than the state of the art curve illustrated by curve 52.

The result obtained after the interpolation step is an interpolated curve giving the diffusion and/or absorption value as a function of the concentration for each type of binary mix.

For example, in the case of a foundation, a first curve is obtained for the red pigment in white pigment mix, a second curve is obtained for the red pigment in black pigment mix, a third curve is obtained for the white pigment in black pigment mix, a fourth curve is obtained for the white pigment in yellow pigment mix, and a fifth curve is obtained for the black pigment in yellow pigment mix.

More generally, the interpolation step is a special case of a step using a physicochemical model capable of predicting interactions between pigments passing through experimental points to obtain the curve giving the diffusion and/or absorption for each wavelength as a function of the given concentration of pigment in the mix of pigments considered.

Interpolation of experimental points is a particular example of a physicochemical model capable of predicting interactions between pigments.

Only the example with piecewise linear interpolation is described in the following for simplification reasons, the transposition to curves obtained with another physicochemical model capable of predicting interactions between pigments being made immediately.

The diffusion and/or absorption curve of the cosmetic product is calculated using interpolated curves.

This is done by calculating the diffusion and/or absorption curve for a mix of colored pigment, black pigment and white pigment, for each colored pigment.

A three segment interpolation is then made for each colored pigment.

This is done by determining the compositions of three binary mixes of pigments obtained in the absence of the third pigment in the mix of colored pigment, black pigment and white pigment.

Such a determination is made for example using projections on a right-angle triangle, each side representing the composition of one pigment.

For example, the two sides of the right-angle triangle correspond to the composition of black pigment and the composition of white pigment, while the hypotenuse corresponds to the composition of colored pigment.

The diffusion and/or absorption value for each binary mix can then be determined using a corresponding interpolated curve.

Three distinct values for diffusion and/or absorption are thus obtained.

Finally, the diffusion and/or absorption value is determined for the mix of colored pigment, black pigment and white pigment by calculating an average of three determined values.

For example, the average is a weighted average.

Thus, according to the illustrated example, the average is weighted by the inverse of the size of the segment (or by the separation in the case of two pigments).

When the composition comprises several colored pigments, interactions between colored segments are neglected so that the operation can be reduced to the case of a plurality of mixes of three pigments.

The calculation step then includes a weighted addition for each colored pigment on the diffusion and/or absorption curve of a mix of colored pigment, black pigment and white pigment, the weighting depending on the relative quantity of colored pigment.

Thus, the diffusion and/or absorption curve of the cosmetic product is obtained using interpolated curves.

In the deduction step, the diffuse reflectivity of the cosmetic product is deduced on a skin model from the curve giving the diffusion and/or absorption curve. The deduction step is made using a Kubelka-Munk model to obtain the diffuse reflectivity from the curve giving the diffusion and/or absorption.

The Kubelka-Munk model is a two-flow model that relates the diffuse reflectivity of a pigment mix with its diffusion and its absorption. The main approximations related to this model are that light propagates only by diffusion in the layer of cosmetic product, and that surface phenomena (related to discontinuity of the optical index and the surface condition) are neglected.

According to one embodiment, the Kubelka-Munk model is a corrected Kubelka-Munk model.

For example, the Kubelka-Munk model is a Kubelka-Munk model corrected using Saunderson corrections.

The Kubelka-Munk model is a particular example of a color model, but any color model can be used in the deduction step.

In the production step, the color of the cosmetic product is obtained on a skin model from the deduced diffuse reflectivity.

For example, the color is obtained by determining the lightness L and the parameters $a^*$ and $b^*$.

Such a determination is implemented by integration operations.

The result obtained at the end of the process is a correspondence between a chemical composition and a color rendering of the cosmetic product applied on skin The quality of the proposed correspondence is better than it is in the state of the art.

The result is that a professional using this correspondence will able to better determine what the rendering of a given composition will look like.

This makes it possible to increase the wearer's satisfaction rate on presentation of a first sample of the cosmetic product adapted to the wearer's skin color.

Therefore the purpose of all these processes and products is to increase the wearer's satisfaction rate on presentation of a first sample of the cosmetic product adapted to the wearer's skin color.

Consequently, the embodiments described above can be combined to form new embodiments, provided that they are technically compatible.

The invention claimed is:

1. A method for determining the color of a cosmetic product on a skin model, the method including steps to:
   supply the composition of pigments in the cosmetic product, the composition comprising at least two pigments including at least one colored pigment,
   for a plurality of wavelengths, supply of experimental points giving diffusion and/or absorption values for several mixes of a given concentration of one pigment in another pigment, each mix corresponding to different given concentrations,
   use of a physicochemical model capable of predicting interactions between pigments passing through experimental points to obtain the curve giving the diffusion and/or absorption for each wavelength as a function of the given concentration of pigment in the mix of pigments considered, the physicochemical model for example being an interpolation of experimental points,
   calculation of the diffusion and/or absorption curve of the cosmetic product using the curves obtained,
   deduction of the diffuse reflectivity of the cosmetic product on a skin model from the curve giving the diffusion and/or absorption, and
   obtaining the color of the cosmetic product on a skin model using the deduced diffuse reflectivity.

2. The method according to claim 1, in which in the supply step, the experimental products are obtained on a skin model.

3. The method according to claim 1, in which the deduction step includes the use of a colorimetric model to obtain the diffuse reflectivity.

4. The method according to claim 1, in which the color is obtained from integrations of the diffuse reflectivity.

5. The method according to claim 1, in which the calculation step includes the calculation of the diffusion and/or absorption curve of a mix of a colored pigment in one or several other pigments, for each colored pigment.

6. The method according to claim 1, in which the calculation step comprises:
   determination of compositions of three binary mixes of pigments obtained in the absence of another pigment in the mix of the colored pigment and the other pigment(s),
   determination of the diffusion and/or absorption value of each binary mix using the curve obtained, and
   determination of the diffusion and/or absorption value for the mix of colored pigment and/or other pigments by calculating an average of three determined values.

7. The method according to claim 1, in which, when the composition includes several colored pigments, the calculation step includes a weighted addition for each colored pigment on the diffusion and/or absorption curve of a mix of the colored pigment and the one or more other pigments, the weighting depending on the relative quantity of colored pigment.

8. The method according to claim 1, in which the method includes the supply of more than four points per mix.

9. The method according to claim 1, in which the points are equally distributed at given concentration.

10. A computer program comprising a legible information support on which a computer program is stored containing program instructions, the computer program being loadable onto a data processing unit and adapted to implement a method of determination according to claim 1 when the computer program is installed on the data processing unit.

11. The method according to claim 3, wherein the colorimetric model is a Kubelka-Munk model corrected using Saunderson corrections.

12. The method according to claim 2, in which the deduction step includes the use of a colorimetric model to obtain the diffuse reflectivity.

13. The method according to claim 2, in which the color is obtained from integrations of the diffuse reflectivity.

14. The method according to claim 3, in which the color is obtained from integrations of the diffuse reflectivity.

15. The method according to claim 2, in which the calculation step includes the calculation of the diffusion and/or absorption curve of a mix of a colored pigment in one or several other pigments, for each colored pigment.

16. The method according to claim 3, in which the calculation step includes the calculation of the diffusion and/or absorption curve of a mix of a colored pigment in one or several other pigments, for each colored pigment.

17. The method according to claim 4, in which the calculation step includes the calculation of the diffusion and/or absorption curve of a mix of a colored pigment in one or several other pigments, for each colored pigment.

18. The method according to claim 2, in which the calculation step comprises:
   determination of compositions of three binary mixes of pigments obtained in the absence of another pigment in the mix of the colored pigment and the other pigment(s),
   determination of the diffusion and/or absorption value of each binary mix using the curve obtained, and
   determination of the diffusion and/or absorption value for the mix of colored pigment and/or other pigments by calculating an average of three determined values.

19. The method according to claim 3, in which the calculation step comprises:
   determination of compositions of three binary mixes of pigments obtained in the absence of another pigment in the mix of the colored pigment and the other pigment(s),
   determination of the diffusion and/or absorption value of each binary mix using the curve obtained, and
   determination of the diffusion and/or absorption value for the mix of colored pigment and/or other pigments by calculating an average of three determined values.

20. The method according to claim 4, in which the calculation step comprises:

determination of compositions of three binary mixes of pigments obtained in the absence of another pigment in the mix of the colored pigment and the other pigment(s), determination of the diffusion and/or absorption value of each binary mix using the curve obtained, and determination of the diffusion and/or absorption value for the mix of colored pigment and/or other pigments by calculating an average of three determined values.

* * * * *